United States Patent

Nakagawa et al.

Patent Number: 5,100,888
Date of Patent: Mar. 31, 1992

[54] CYCLIC AMIDINYLTHIOCARBAPENEM DERIVATIVES

[75] Inventors: Susumu Nakagawa; Yoshiaki Kato; Hiroshi Fukatsu, all of Aichi, Japan

[73] Assignee: Banyu Pharmaceutical Co., Ltd., Tokyo, Japan

[21] Appl. No.: 549,574

[22] Filed: Jul. 6, 1990

[30] Foreign Application Priority Data

Jul. 6, 1989 [JP] Japan .................. 1-174680

[51] Int. Cl.$^5$ .................. C07D 487/04; A61K 31/40
[52] U.S. Cl. ......................... 514/210; 540/350
[58] Field of Search ............... 540/350; 514/210

[56] References Cited

FOREIGN PATENT DOCUMENTS 0126587 11/1984 European Pat. Off. .
0144825  6/1985 European Pat. Off. .
0256377  2/1988 European Pat. Off. .
60-178888 9/1985 Japan ................... 540/350

Primary Examiner—Robert Gerstl
Attorney, Agent, or Firm—Sughrue, Mion, Zinn, Macpeak & Seas

[57] ABSTRACT

A compound represented by formula (I):

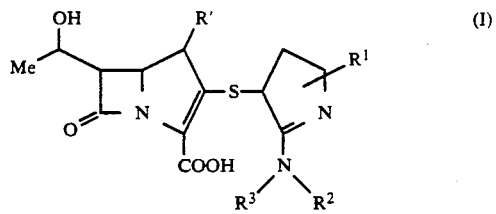

wherein $R^1$ represents a hydrogen atom or a methyl group; $R^2$ and $R^3$, which may be the same or different, each represents a hydrogen atom or a lower alkyl group; and $R^4$ represents a carboxyl group, a lower alkoxycarbonyl group, a carbamoyl group, a lower alkylcarbamoyl group, a di-lower alkylcarbamoyl group, or a carbonyl group substituted with a heterocyclic group selected from the group consisting of an aziridinyl group, an azetidinyl group, a pyrrolidinyl group, a piperidino group, a morpholino group, a thiomorpholino group, a piperazinyl group, and a 4-lower alkyl-1-piperazinyl group, or a pharmaceutically acceptable salt or ester thereof. The compound of formula (I) and their salts or esters exhibit excellent antibacterial activity.

6 Claims, No Drawings

CYCLIC AMIDINYLTHIOCARBAPENEM DERIVATIVES

FIELD OF THE INVENTION

This invention relates to a novel carbapenem derivative useful as a treating agent of bacterial infectious diseases in the field of pharmaceuticals.

BACKGROUND OF THE INVENTION

Since thienamycin having useful activities as an antibiotic was discovered, a number of carbapenem derivatives have been synthesized and applied for patents Prior art relevant to the present invention is found, for example, in U.S. Pat. Nos. 4,696,923 and 4,717,728. The carbapenem derivatives disclosed in U.S. Pat. No. 4,696,923 have a 3-azetidinylthio group, a 3-pyrrolidinylthio group, a 4-piperidylthio group, etc. whose N-atom is substituted with a substituted amidino group, a formimidoyl- group, etc. at the 2-position of the carbapenem skeleton However, these compounds are confined to those in which the heterocyclic moiety of the heterocyclic thio group is saturated and carries no substituent on its carbon atoms. On the other hand, U.S. Pat. No. 4,717,728 discloses carbapenem compounds having a cyclic amidinylthio group at the 2-position of the carbapenem skeleton. The cyclic amidinyl group or cyclic guanidinyl group of these compounds has no substituent on the ring-forming carbon atoms and is limited to a 2-imino-1-(substituted or unsubstituted)-piperidin-3-ylthio group.

Besides, both the above-described relevant references give no specific antimicrobial spectral data of their typical compounds.

While carbapenem derivatives are useful for the treatment of human and animal diseases caused by pathogenic bacteria, antibacterial activities of the state-of-the-art carbapenem derivatives are not sufficiently satisfactory, and there has been a demand to develop a compound exhibiting excellent antibacterial activities against various pathogenic bacteria.

Imipenem, a carbapenem compound now clinically used, is decomposed by renal dehydropeptidase (hereinafter abbreviated as DHP) similarly to thienamycin, so that it is used in combination with a DHP inhibitor, e.g., cilastatin. Hence, a carbapenem compound having improved stability against DHP as well as satisfactory antibacterial activity has been demanded.

SUMMARY OF THE INVENTION

The inventors have conducted extensive investigations to develop a carbapenem derivative having excellent antibacterial activity against various pathogenic bacteria. As a result, it has now been found that a novel carbapenem derivative represented by formula (I) shown below shows excellent antibacterial activity and reached the present invention.

That is, the present invention relates to a compound represented by formula (I):

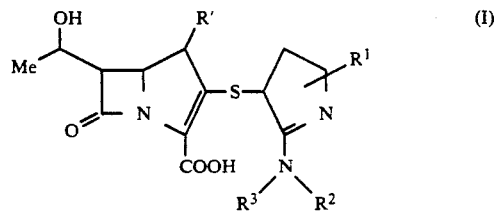

wherein $R^1$ represents a hydrogen atom or a methyl group; $R^2$ and $R^3$, which may be the same or different, each represents a hydrogen atom or a lower alkyl group; and $R^4$ represents a carboxyl group, a lower alkoxycarbonyl- group, a carbamoyl group, a lower alkylcarbamoyl group, a di-lower alkylcarbamoyl group, or a carbonyl group substituted with a heterocyclic group selected from the group consisting of an aziridinyl group, an azetidinyl group, a pyrrolidinyl group, a piperidino group, a morpholino group, a thiomorpholino group, a piperazinyl group, and a 4-lower alkyl-1-piperazinyl group, or a pharmaceutically acceptable salt or ester thereof.

The present invention also relates to a process for preparing the compound of formula (I) or a pharmaceutically acceptable salt or ester thereof.

The present invention further relates to an antibacterial agent containing the compound of formula (I) or a pharmaceutically acceptable salt or ester thereof as an active ingredient.

The present invention furthermore relates to a compound represented by formula (II):

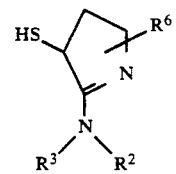

wherein $R^2$ and $R^3$ are as defined above; $R^6$ represents a carboxyl group, a protected carboxyl group, a lower alkoxycarbonyl group, a carbamoyl group, a lower alkylcarbamoyl group, a di-lower alkylcarbamoyl group, or a carbonyl group substituted with a heterocyclic group selected from the group consisting of an aziridinyl group, an azetidinyl group, a pyrrolidinyl group, a piperidino group, a morpholino group, a thiomorpholino group, a piperazinyl group, and a 4-lower alkyl-1-piperazinyl group.

The compound represented by formula (II) is an important intermediate for synthesizing the compound of formula (I).

DETAILED DESCRIPTION OF THE INVENTION

The terminology "lower" as used herein means that the group following "lower" contains from 1 to 6 carbon atoms That is, "lower alkyl group" includes methyl, ethyl, n-propyl, isopropyl, n-butyl, isobutyl, t-butyl, n-pentyl, n-hexyl, and isohexyl groups Preferred of them are those containing from 1 to 4 carbon atoms, e.g., methyl, ethyl, n-propyl, n-butyl, and t-butyl groups.

The terminology "lower alkoxycarbonyl group" as used herein means an oxycarbonyl group substituted with the above-described lower alkyl group and includes, for example, methoxycarbonyl, ethoxycarbonyl, n-propoxycarbonyl, and t-butoxycarbonyl groups. Preferred of them are those having from 2 to 5 carbon atoms, e.g., methoxycarbonyl, ethoxycarbonyl, and t-butoxycarbonyl groups.

The terminology "lower alkylcarbamoyl group" as used herein means a carbamoyl group substituted with the above-described lower alkyl group and preferably includes those having from 2 to 5 carbon atoms, e.g., methylcarbamoyl, ethylcarbamoyl, isopropylcarbamoyl, and t-butylcarbamoyl groups.

The terminology "di-lower alkylcarbamoyl group" as used herein means a carbamoyl group disubstituted with the above-described lower alkyl group and preferably includes those having from 3 to 7 carbon atoms, .e g., dimethylcarbamoyl, diethylcarbamoyl, and ethylmethylcarbamoyl groups.

$R^1$ represents a hydrogen atom or a methyl group, and preferably a methyl group.

$R^2$ and $R^3$, which may be the same or different, each represents a hydrogen atom or a lower alkyl group. When $R^2$ is a hydrogen atom, $R^3$ preferably represents a hydrogen atom, a methyl group, or an ethyl group. When $R^1$ is a methyl group, $R^3$ preferably represents a methyl group or an ethyl group. When $R^2$ is an ethyl group, $R^3$ preferably represents an ethyl group.

$R^4$ represents a carboxyl group, a lower alkoxycarbonyl group, a carbamoyl group, a lower alkylcarbamoyl group, a di-lower alkylcarbamoyl group, or a carbonyl group substituted with a heterocyclic group selected from the group consisting of an aziridinyl group, an azetidinyl group, a pyrrolidinyl group, a piperidino group, a morpholino group, a thiomorpholino group, a piperazinyl group, and a 4-lower alkyl-1-piperazinyl group. $R^1$ preferably represents a carbamoyl group, a methylcarbamoyl group, an ethylcarbamoyl group, an isopropylcarbamoyl group, a dimethylcarbamoyl group, a diethylcarbamoyl group, an ethylmethylcarbamoyl group, a 1-aziridinylcarbonyl group, a 1-azetidinylcarbonyl group, a 1-pyrrolidinylcarbonyl group, a piperidinocarbonyl group, a morpholinocarbonyl group, a thiomorpholinocarbonyl group, a 1-piperazinylcarbonyl group, or a 4-methyl-1-piperazinylcarbonyl The compounds of formula (I) wherein at least one of $R^2$ and $R^3$ is a hydrogen atom show tautomerism at the 2-positioned side chain thereof, an example where $R^3$ is a hydrogen atom being illustrated below.

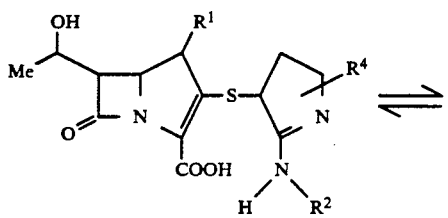

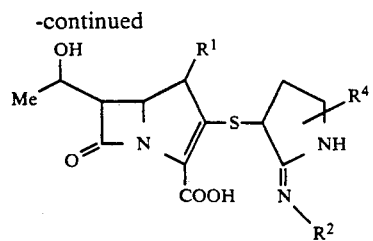

The compounds of formula (I) also embrace steric isomers ascribed to asymmetric carbon atoms on the pyrrolidin-3-ylthio ring at the 2-position of the carbapenem skeleton.

The compounds of formula (I) further include steric isomers ascribed to asymmetric carbon atoms at the 1-, 5-, 6-, and 8-positions of the carbapenem skeleton.

Of these isomers, preferred are those compounds having a (5R,6S)-configuration similar to the structure of thienamycin and also having the 8-positioned carbon atom in an R-configuration, i.e., those having a (5R,6S,8R)-configuration and, where the 1-position is substituted with a methyl group, those having a (1R,5S,6S,8R)-configuration.

Accordingly, preferred of the compounds of formula (I) are those represented by formulae (I-a) and (I-b):

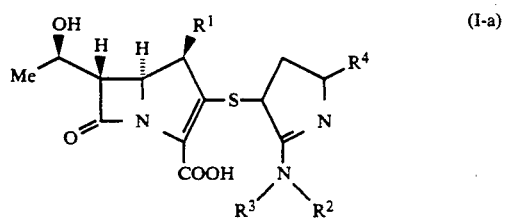

wherein $R^1$, $R^2$, $R^3$ and $R^4$ are defined above.

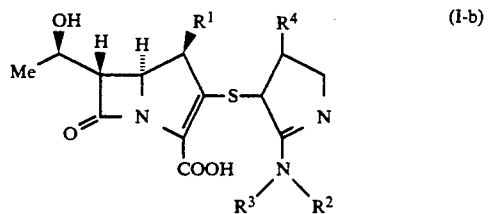

wherein $R^1$, $R^2$, $R^3$, and $R^4$ are as defined above.

Inter alia, the compounds of formula (I-a) are preferred.

Specific examples of the compounds of formula (I) are shown below.

| Compound number | $R^1$ | $R^2$ | $R^3$ | $R^4$ |
|---|---|---|---|---|

[structure shown with $CH_3$, OH, $R^1$, S, $R^4$, COOH, N, $R^2$, $R^3$]

| (1) | H | H | H | $CON(CH_3)_2$ |
| (2) | H | H | H | $CON(C_2H_5)_2$ |

-continued

| Compound number | R¹ | R² | R³ | R⁴ |
|---|---|---|---|---|
| (3) | H | H | H | CON(CH$_3$)C$_2$H$_5$ |
| (4) | H | H | H | CONH$_2$ |
| (5) | H | H | H | CONHCH$_3$ |
| (6) | H | H | H | CONHC$_2$H$_5$ |
| (7) | H | H | H | CONHC$_3$H$_7^i$ |
| (8) | H | H | H | CON-(cyclopropyl) |
| (9) | H | H | H | CON-(azetidinyl) |
| (10) | H | H | H | CON-(pyrrolidinyl) |
| (11) | H | H | H | CON-(piperidinyl) |
| (12) | H | H | H | CON-(morpholinyl) |
| (13) | H | H | H | CON-(piperazinyl-NH) |
| (14) | H | H | H | CON-(N-methylpiperazinyl) |
| (15) | CH$_3$ | H | H | CON(CH$_3$)$_2$ |
| (16) | CH$_3$ | H | H | CON(C$_2$H$_5$)$_2$ |
| (17) | CH$_3$ | H | H | CON(CH$_3$)C$_2$H$_5$ |
| (18) | CH$_3$ | H | H | CONH$_2$ |
| (19) | CH$_3$ | H | H | CONHCH$_3$ |
| (20) | CH$_3$ | H | H | CONHC$_2$H$_5$ |
| (21) | CH$_3$ | H | H | CONHC$_3$H$_7^i$ |
| (22) | CH$_3$ | H | H | CON-(cyclopropyl) |
| (23) | CH$_3$ | H | H | CON-(azetidinyl) |
| (24) | CH$_3$ | H | H | CON-(pyrrolidinyl) |
| (25) | CH$_3$ | H | H | CON-(piperidinyl) |
| (26) | CH$_3$ | H | H | CON-(morpholinyl) |
| (27) | CH$_3$ | H | H | CON-(piperazinyl-NH) |
| (28) | CH$_3$ | H | H | CON-(N-methylpiperazinyl) |
| (29) | H | CH$_3$ | CH$_3$ | CON(CH$_3$)$_2$ |
| (30) | H | CH$_3$ | CH$_3$ | CON(C$_2$H$_5$)$_2$ |
| (31) | H | CH$_3$ | CH$_3$ | CON(CH$_3$)C$_2$H$_5$ |
| (32) | H | CH$_3$ | CH$_3$ | CONH$_2$ |
| (33) | H | CH$_3$ | CH$_3$ | CONHCH$_3$ |
| (34) | H | CH$_3$ | CH$_3$ | CONHC$_2$H$_5$ |
| (35) | H | CH$_3$ | CH$_3$ | CONHC$_3$H$_7^i$ |
| (36) | H | CH$_3$ | CH$_3$ | CON-(cyclopropyl) |
| (37) | H | CH$_3$ | CH$_3$ | CON-(azetidinyl) |
| (38) | H | CH$_3$ | CH$_3$ | CON-(pyrrolidinyl) |
| (39) | H | CH$_3$ | CH$_3$ | CON-(piperidinyl) |
| (40) | H | CH$_3$ | CH$_3$ | CON-(morpholinyl) |
| (41) | H | CH$_3$ | CH$_3$ | CON-(piperazinyl-NH) |
| (42) | H | CH$_3$ | CH$_3$ | CON-(N-methylpiperazinyl) |
| (43) | CH$_3$ | CH$_3$ | CH$_3$ | CON(CH$_3$)$_2$ |
| (44) | CH$_3$ | CH$_3$ | CH$_3$ | CON(C$_2$H$_5$)$_2$ |
| (45) | CH$_3$ | CH$_3$ | CH$_3$ | CON(CH$_3$)C$_2$H$_5$ |
| (46) | CH$_3$ | CH$_3$ | CH$_3$ | CONH$_2$ |
| (47) | CH$_3$ | CH$_3$ | CH$_3$ | CONHCH$_3$ |
| (48) | CH$_3$ | CH$_3$ | CH$_3$ | CONHC$_2$H$_5$ |
| (49) | CH$_3$ | CH$_3$ | CH$_3$ | CONHC$_3$H$_7^i$ |
| (50) | CH$_3$ | CH$_3$ | CH$_3$ | CON-(cyclopropyl) |

-continued

| Compound number | R¹ | R² | R³ | R⁴ |
|---|---|---|---|---|
| (51) | CH₃ | CH₃ | CH₃ | CON⟨azetidine⟩ |
| (52) | CH₃ | CH₃ | CH₃ | CON⟨pyrrolidine⟩ |
| (53) | CH₃ | CH₃ | CH₃ | CON⟨piperidine⟩ |
| (54) | CH₃ | CH₃ | CH₃ | CON⟨morpholine⟩ |
| (55) | CH₃ | CH₃ | CH₃ | CON⟨piperazine-NH⟩ |
| (56) | CH₃ | CH₃ | CH₃ | CON⟨piperazine-N-CH₃⟩ |
| (57) | CH₃ | H | H | CON⟨thiomorpholine⟩ |
| (58) | CH₃ | CH₃ | CH₃ | CON⟨thiomorpholine⟩ |
| (59) | CH₃ | CH₃ | H | CON(CH₃)₂ |
| (60) | CH₃ | CH₃ | H | CONH₂ |

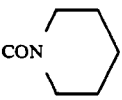

| (61) | H | H | H | CON(CH₃)₂ |
| (62) | H | H | H | CON(C₂H₅)₂ |
| (63) | H | H | H | CON(CH₃)C₂H₅ |
| (64) | H | H | H | CONH₂ |
| (65) | H | H | H | CONHCH₃ |
| (66) | H | H | H | CONHC₂H₅ |
| (67) | H | H | H | CONHC₃H₇ⁱ |
| (68) | H | H | H | CON⟨aziridine⟩ |
| (69) | H | H | H | CON⟨azetidine⟩ |
| (70) | H | H | H | CON⟨pyrrolidine⟩ |
| (71) | H | H | H | CON⟨piperidine⟩ |
| (72) | H | H | H | CON⟨morpholine⟩ |
| (73) | H | H | H | CON⟨piperazine-NH⟩ |
| (74) | H | H | H | CON⟨piperazine-N-CH₃⟩ |
| (75) | CH₃ | H | H | CON(CH₃)₂ |
| (76) | CH₃ | H | H | CON(C₂H₅)₂ |
| (77) | CH₃ | H | H | CON(CH₃)₂C₂H₅ |
| (78) | CH₃ | H | H | CONH₂ |
| (79) | CH₃ | H | H | CONHCH₃ |
| (80) | CH₃ | H | H | CONHC₂H₅ |
| (81) | CH₃ | H | H | CONHC₃H₇ⁱ |
| (82) | CH₃ | H | H | CON⟨aziridine⟩ |
| (83) | CH₃ | H | H | CON⟨azetidine⟩ |
| (84) | CH₃ | H | H | CON⟨pyrrolidine⟩ |
| (85) | CH₃ | H | H | CON⟨piperidine⟩ |
| (86) | CH₃ | H | H | CON⟨morpholine⟩ |
| (87) | CH₃ | H | H | CON⟨piperazine-NH⟩ |
| (88) | CH₃ | H | H | CON⟨piperazine-N-CH₃⟩ |
| (89) | H | CH₃ | CH₃ | CON(CH₃)₂ |
| (90) | H | CH₃ | CH₃ | CON(C₂H₅)₂ |

-continued

| Compound number | R¹ | R² | R³ | R⁴ |
|---|---|---|---|---|
| (91) | H | CH₃ | CH₃ | CON(CH₃)C₂H₅ |
| (92) | H | CH₃ | CH₃ | CONH₂ |
| (93) | H | CH₃ | CH₃ | CONHCH₃ |
| (94) | H | CH₃ | CH₃ | CONHC₂H₅ |
| (95) | H | CH₃ | CH₃ | CONHC₃H₇ⁱ |
| (96) | H | CH₃ | CH₃ | CON–△ |
| (97) | H | CH₃ | CH₃ | CON–◇ |
| (98) | H | CH₃ | CH₃ | CON–(5-ring) |
| (99) | H | CH₃ | CH₃ | CON–(6-ring) |
| (100) | H | CH₃ | CH₃ | CON–(6-ring)–O |
| (101) | H | CH₃ | CH₃ | CON–(6-ring)–NH |
| (102) | H | CH₃ | CH₃ | CON–(6-ring)–N–CH₃ |
| (103) | CH₃ | CH₃ | CH₃ | CON(CH₃)₂ |
| (104) | CH₃ | CH₃ | CH₃ | CON(C₂H₅)₂ |
| (105) | CH₃ | CH₃ | CH₃ | CON(CH₃)C₂H₅ |
| (106) | CH₃ | CH₃ | CH₃ | CONH₂ |
| (107) | CH₃ | CH₃ | CH₃ | CONHCH₃ |
| (108) | CH₃ | CH₃ | CH₃ | CONHC₂H₅ |
| (109) | CH₃ | CH₃ | CH₃ | CONHC₃H₇ⁱ |
| (110) | CH₃ | CH₃ | CH₃ | CON–△ |
| (111) | CH₃ | CH₃ | CH₃ | CON–◇ |
| (112) | CH₃ | CH₃ | CH₃ | CON–(5-ring) |
| (113) | CH₃ | CH₃ | CH₃ | CON–(6-ring) |
| (114) | CH₃ | CH₃ | CH₃ | CON–(6-ring)–O |
| (115) | CH₃ | CH₃ | CH₃ | CON–(6-ring)–NH |
| (116) | CH₃ | CH₃ | CH₃ | CON–(6-ring)–N–CH₃ |
| (117) | CH₃ | H | H | CON–(6-ring)–S |

The preferred examples of the compound listed above are as follows:

(1) (5R,6S)-2-[(3RS,5S)-5-dimethylcarbamoyl-2-iminopyrrolidin-3-yl]thio-6-[(1R)-1-hydroxyethyl]-1-carbapen-2-em-3-carboxylic acid (2) (5R,6S)-2-[(3RS,5S)-5-diethylcabamoyl-2-iminopyrrolidin-3-yl]thio-6-[(1R)-1-hydroxyethyl]-1-carbapen-2-em-3-carboxylic acid (3) (5R,6S)-2-[(3RS,5S)-5-ethylmethylcarbamoyl-2-iminopyrrolidin-3-yl]thio-6-[(1R)-1-hydroxyethyl]-1-carbapen-2-em-3-carboxylic acid (4) (5R,6S)-2-[(3RS,5S)-5-carbamoyl-2-iminopyrrolidin-3-yl]thio-6-[(1R)-1-hydroxyethyl]-1-carbapen-2-em-3-carboxylic acid (5) (5R,6S)-2-[(3RS,5S)-2-imino-5-methylcarbamoylpyrrolidin-3-yl]thio-6-[(1R)-1-hydroxyethyl]-1-carbapen-2-em-3-carboxylic acid (6) (5R,6S)-2-[(3RS,5S)-5-ethylcarbamoyl-2-iminopyrrolidin-3-yl]thio-6-[(1R)-1-hydroxyethyl]-1-carbapen-2-em-3-carboxylic acid

(15) (1R,5S,6S)-2-[(3RS,5S)-5-dimethylcarbamoyl-2-iminopyrrolidin-3-yl]thio-6-[(1R)-1-hydroxyethyl]-1-methylcarbapen-2-em-3-carboxylic acid

(16) (1R,5S,6S)-2-[(3RS,5S)-5-diethylcarbamoyl-2-iminopyrrolidin-3-yl]thio-6-[(1R)-1-hydroxyethyl]-1-methylcarbapen-2-em-3-carboxylic acid

(17) (1R,5S,6S)-2-[(3RS,5S)-5-ethylmethylcarbamoyl-2-iminopyrrolidin-3-yl]thio-6-[(1R)-1-hydroxyethyl]-1-methylcarbapen-2-em-3-carboxylic acid

(18) (1R.,5S,6S)-2-[(3RS,5S)-5-carbamoyl-2-iminopyrrolidin-3-yl]thio-6-[(1R)-1-hydroxyethyl]-1-methylcarbapen-2-em-3-carboxylic acid

(19) (1R,5S,6S)-2-[(3RS,5S)-2-imino-5-methylcarbamoylpyrrolidin-3-yl]thio-6-[(1R)-1-hydroxyethyl]-1-methylcarbapen-2-em-3-carboxylic acid

(20) (1R,5S,6S)-2-[(3RS,5S)-5-ethylcarbamoyl-2-iminopyrrolidin-3-yl]thio-6-[(1R)-1-hydroxyethyl]-1-methylcarbapen-2-em-3-carboxylic acid

(29) (5R,6S)-2-[(3RS,5S)-2-dimethylamino-5-dimethylcarbamoyl-1-pyrrolin-3-yl]thio-6-[(1R)-1-hydroxyethyl]-1-carbapen-2-em-3-carboxylic acid

(30) (5R,6S)-2-[(3RS,5S)-5-diethylcarbamoyl-2-dimethylamino-1-pyrrolin-3-yl]thio-6[(1R)-1-hydroxyethyl]-1-carbapen-2-em-3-carboxylic acid

(31) (5R,6S)-2-[(3RS,5S)-2-dimethylamino-5-ethylmethylcarbamoyl-1-pyrrolin-3-yl]thio-6-[(1R)-1-hydroxyethyl]-1-carbapen-2-em-3-carboxylic acid

(32) (5R,6S)-2-[(3RS,5S)-5-carbamoyl-2-dimethylamino-1-pyrrolin-3-yl]thio-6-[(1R)-1-hydroxyethyl]-1-carbapen-2-em-3-carboxylic acid

(33) (5R,6S)-2-[(3RS,5S)-2-dimethylamino-5-methylcarbamoyl-1-pyrrolin-3-yl]thio-6-[(1R)-1-hydroxyethyl]-1-carbapen-2-em-3-carboxylic acid

(34) (5R,6S)-2-[(3RS,5S)-2-dimethylamino-5-ethylcarbamoyl-1-pyrrolin-3-yl]thio-6-[(1R)-1-hydroxyethyl]-1-carbapen-2-em-3-carboxylic acid

(35) (5R,6S)-2-[(3RS,5S)-2-dimethylamino-5-isopropylcarbamoyl-1-pyrrolin-3-yl]thio-6-[(1R)-1-hydroxyethyl]-1-carbapen-2-em-3-carboxylic acid

(43) (1R,5S,6S)-2-[(3RS,5S)-2-dimethylamino-5-dimethylcarbamoyl-1-pyrrolin-3-yl-]thio-6-[(1R)-1-hydroxyethyl]-1-methylcarbapen-2-em-3-carboxylic acid

(44) (1R,5S,6S)-2-[(3RS,5S)-5-diethylcarbamoyl-2-dimethylamino-1-pyrrolin-3-yl]thio-6-[(1R)-1-hydroxyethyl]-1-methylcarbapen-2-em-3-carboxylic acid

(45) (1R,5S,6S)-2-[(3RS,5S)-2-dimethylamino-5-ethylmethylcarbamoyl-1-pyrrolin-3-yl]thio-6-[(1R)-hydroxyethyl]-1-methylcarbapen-2-em-3-carboxylic acid

(46) (1R,5S,6S)-2-[(3RS,5S)-5-carbamoyl-2-dimethylamino-1-pyrrolin-3-yl]thio-6-[(1R)-1-hydroxyethyl]-1-methylcarbapen-2-em-3-carboxylic acid

(47) (1R,5S,6S)-2-[(3RS,5S)-2-dimethylamino-5-methylcarbamoyl-1-pyrrolin-3-yl]thio-6-[(1R)-1-hydroxyethyl]-1-methylcarbapen-2-em-3-carboxylic acid

(48) (1R,5S,6S)-2-[(3RS,5S)-2-dimethylamino-5-ethylcarbamoyl-1-pyrrolin-3-yl]thio-6-[(1R)-1-hydroxyethyl]-1-methylcarbapen-2-em-3-carboxylic acid

(59) (1R,5S,6S)-2-[(3RS,5S)-dimethylcarbamoyl-2-methylamino-1-pyrrolin-3-yl]thio-6-[(1R)-1-hydroxyethyl]-1-methylcarbapen-2-em-3-carboxylic acid

(60) (1R,5S,6S)-2-[(3RS,5S)-5-carbamoyl-2-methylamino-1-pyrrolin-3-yl]thio-6-[(1R)-1-hydroxyethyl]-1-methylcarbapen-2-em-3-carboxylic acid.

Especially the compounds of (1), (4), (15), (18), (29), (30), (32), (43) and (46) are preferred among the above compounds.

The compounds of formula (I) can be converted to pharmaceutically acceptable non-toxic salts or esters thereof in a usual manner.

Non-toxic salts of the compounds of formula (I) are those pharmaceutically acceptable and commonly employed, i.e., salts formed at the carboxyl group at the 3-position of the carbapenem skeleton or on the nitrogen atom on the pyrrolidine ring at the 2-position of the carbapenem skeleton. Examples of such salts include salts with alkali metals, e.g., sodium, potassium, and lithium; salts with alkaline earth metals, e.g., calcium and magnesium; salts with organic amines, e.g., N,N'-dibenzylethylenediamine, ethanolamine, and triethylamine; salts with inorganic acids, e.g., hydrochloric acid, nitric acid, sulfuric acid, and phosphoric acid; salts with organic acids, e.g., citric acid and tartaric acid; salts with organic sulfonic acids, e.g., methanesulfonic acid and p-toluenesulfonic acid; and salts with amino acids, e.g., aspartic acid, glutamic acid, and lysine.

Non-toxic esters of the compounds of formula (I) are those pharmaceutically acceptable and commonly employed which are formed at the carboxyl group at the 3-position of the carbapenem skeleton or the carboxyl group on the pyrroline ring at the 2-position of the carbapenem skeleton. Examples of such esters include esters with an alkanoyloxymethyl group, e.g., acetoxymethyl and pivaloyloxymethyl groups; esters with an alkoxycarbonyloxyalkyl group, e.g., a 1-(ethoxycarbonyloxy)ethyl group; esters with a phthalidyl group; and esters with a 5-substituted-2-oxo-1,3-dioxol-4-ylmethyl group, e.g., a 5-methyl-2-oxo-1,3-dioxol-4-ylmethyl group.

The compound of formula (I) can be prepared by reacting a compound represented by formula (III):

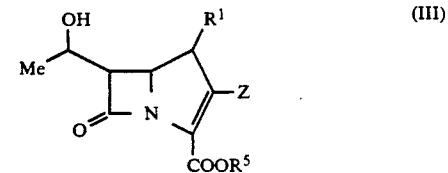

wherein $R^1$ is as defined above; $R^5$ represents a carboxyl-protective group; and Z represents a leaving group, with a compound represented by formula (II) as defined above, and removing the protective group(s).

The reaction between the compound of formula (II) and the compound of formula (III) can be carried out in an inert solvent giving no adverse influence on the reaction, such as acetonitrile, N,N-dimethylformamide, dimethylacetamide, and N-ethylpyrrolidine, in the presence of a base, e.g., diisopropylethylamine, triethylamine, and 4-dimethylaminopyridine, at a temperature of from $-40°$ to $25°$ C. for a period of from 5 minutes to 10 hours.

In formula (III), the leaving group represented by Z means an acyl group derived from an organic phosphoric acid or an organic sulfonic acid. Examples of suitable leaving groups include diphenylphosphoryloxy, methanesulfonyloxy, trifluoromethanesulfonyloxy, and p-toluene-sulfonyloxy groups, with diphenylphosphoryloxy and methanesulfonyloxy groups being preferred.

In formula (II), where $R^2$ and $R^3$ both represent a hydrogen atom, the amino group at the 2-position of the pyrroline skeleton may be protected prior to the reaction.

Protective groups for the amino group or carboxyl group may be any of those usually employed in the art. These protective groups can be removed by well-known reactions for removal of protective groups to yield the desired compound of formula (I).

In typical examples, when the amino-protective group is a p-nitrobenzyloxycarbonyl group, and the carboxyl-protective group is a p-nitrobenzyl group, these protective groups can be removed by treating the reaction product in a mixed solvent (e.g., tetrahydrofuran-water, dioxane-ethanol-water, and butanol-water) containing a phosphoric acid buffer, a 3-morpholinopropanesulfonic acid buffer, dipotassium phosphate, etc. (pH=7) in the presence of a catalyst for hydrogenation, e.g., palladium-on-activated carbon, palladium hydroxide, and platinum oxide, at a hydrogen pressure of from 1 to 4 atm. and at a temperature of from 0° to 50° C. for a period of from 20 minutes to 4 hours. When the amino-protective group is an allyloxycarbonyl group, and the carboxyl-protective group is an allyl group, these protective groups can be removed by treating the reaction product in an inert solvent (e.g., tetrahydrofuran, diethyl ether, and dichloromethane) in the presence of a catalyst comprising a palladium compound and triphenylphosphine.

The compound of formula (III) can be synthesized from bicyclic keto esters according to, for example, the process disclosed in T. N. Salzmann et al., *J. Am. Chem. Soc.*, Vol. 102, p. 6161 (1980) or D. H. Shih et al., *Heterocycles*, Vol. 21, p. 29 (1984) or analogues thereof. The compound thus synthesized can be used for the reaction with the compound of formula (II) without being isolated from the reaction mixture.

The compound of formula (II) is an unreported novel compound, serving as an important intermediate for preparing the compound of formula (I).

Hence, the present invention also relates to a compound represented by formula (II) as defined above, and a process for preparing the same.

Of the compounds of formula (II), preferred are those represented by formula (II$_1$):

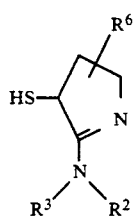

wherein $R^2$, $R^3$, and $R^6$ are as defined above.

More preferred are those represented by formula (II$_1$-a):

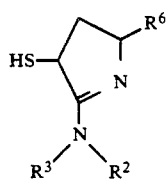

wherein $R^2$, $R^3$, and $R^6$ are as defined above.

The compound of formula (II) can be prepared, for example, through the following reaction scheme:

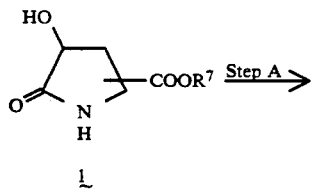

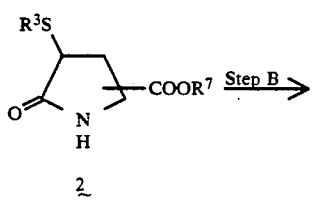

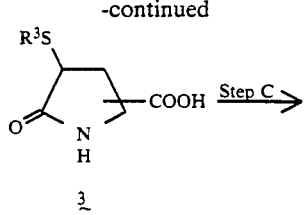

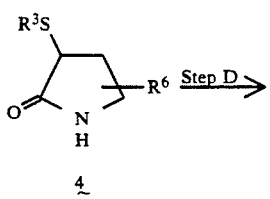

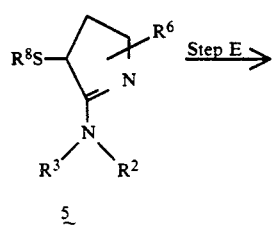

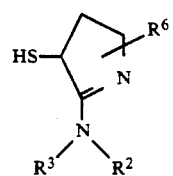

wherein $R^2$, $R^3$, and $R^6$ are as defined above; $R^7$ represents a protective group for a carboxyl group; and $R^8$ represents a protective group for a mercapto group.

Step A

Step A can be carried out by various known techniques for converting a hydroxyl group to a protected mercapto group. For example, the hydroxyl group of Compound 1 is converted to an active ester form (e.g., a mesyloxy group and a tosyloxy group) or a halogen atom (e.g., chlorine, bromine, and iodine), and the resulting halogeno derivative or the active ester derivative is then reacted with a reagent for substituting oxygen with sulfur (e.g., thioacetic acid, thiobenzoic acid, tritylmercaptan, and p-methoxybenzylmercaptan) (hereinafter referred to as thio-reagent) in the presence of a base (e.g., triethylamine, diisopropylethylamine, N-methylmorpholine, 1,8-diazabicyclo[5.4.0]-7-undecene (hereinafter abbreviated as DBU), sodium hydroxide, potassium t-butoxide, sodium methoxide, and sodium hydride).

Amounts of reagents to be used are appropriately selected depending on the reaction conditions and the like. Generally, the thio-reagent is used in an amount of from 1 to 5 mols, preferably from 1 to 2 mols, per mol of Compound 1, and the base is used in an amount of from 1 to 5 mols, preferably from 1 to 2 mols, per mol of Compound 1. The reaction can be carried out in an inert solvent giving no adverse influence on the reaction, e.g., dichloromethane, tetrahydrofuran (hereinafter abbreviated as THF), and N,N-dimethylformamide (hereinafter abbreviated as DMF), or a mixture thereof. The reaction temperature usually ranges from −60° to 80° C., and preferably from −20° to room temperature. The reaction time is usually from 15 minutes to 16 hours, and preferably from 30 minutes to 2 hours.

Step A can also be effected by reacting Compound 1 with a thio-reagent, e.g., thioacetic acid, in an inert solvent, e.g., THF, in the presence of triphenylphosphine and diethyl azodicarboxylate. The amount each of triphenylphosphine, diethyl azodicarboxylate, and the thio-reagent to be used suitably ranges from 1 to 5 mols per mol of Compound though somewhat varying depending on the reaction conditions and the like. The reaction is usually conducted at a temperature of from 0° to 70° C. for a period of from 15 minutes to 24 hours.

Step B

Step B can be achieved by a process selected according to the kind of the ester residue $COOR^7$ from among various known techniques for converting an ester group to a carboxyl group, for example, alkali hydrolysis, treatment with an acid (e.g., trifluoroacetic acid and hydrobromic acid), catalytic reduction, and a reductive process using zinc, etc.

Step C

When $R^6$ is a protected carboxyl group or a lower alkoxycarbonyl group, Steps B and C may be omitted depending on the kind of $R^7$. When necessary, Step C can be achieved by various known reactions for protection or esterification.

When $R^6$ is a substituted or unsubstituted carbamoyl group, this step can be effected by various known processes for converting a carboxyl group to a carbamoyl group. For example, Compound 3 is converted to its reactive derivative at the carboxyl group, such as an acid chloride, an acid anhydride, and an active ester, and the reactive derivative is then reacted with a desired amine compound in an inert solvent. The amount of the amine compound to be used usually ranges from 1 to 5 mols per mol of Compound though more or less varying depending on the reaction conditions and the like. The reaction is carried out at a temperature of from −20° to 80° C. for a period of from 15 minutes to 24 hours.

Step C may also be performed by reacting Compound 3 with the amine compound in the presence of a condensing agent, e.g., N,N'-dicyclohexylcarbodiimide (hereinafter abbreviated as DCC) and silicon tetrachloride to obtain Compound 4. The reaction is carried out by using from 1 to 5 mols of the amine compound per mol of Compound 3 at a temperature of from 0° to 30° C. for a period of from 1 to 24 hours.

Step D

Step D can be achieved by various known techniques for converting an amide compound to an amidine derivative. For example, the amide compound (Compound 4) is once converted to an imidate intermediate, which is then condensed with a desired amine compound to obtain the amidine derivative (Compound 5). The reaction from the amide compound to the imidate intermediate can be carried out by reacting the amide compound with triethyloxonium tetrafluoroborate in an inert solvent, e.g., dichloromethane, at a temperature of from −20° C. to room temperature for a period of from 30 minutes to 24 hours. Triethyloxgnium tetrafluoroborate may be replaced with dimethyl sulfate, ethyl chloroformate, etc. Triethyloxonium tetrafluoroborate is suitably used in an amount of from 1 to 5 mols per mol of Compound 4. The reaction from the imidate intermediate to an amidine derivative (Compound 5) can be carried out in a solvent giving no adverse influence on the reaction, e.g., methanol and ethanol, at a temperature of from 0° to 80° C. for a period of from 1 to 24 hours. The amine compound is suitably used in an amount of from 1 to 5 mols per mol of Compound 4.

Step D may also be achieved through an imidoyl chloride intermediate or an imidate-like intermediate obtained by reacting with phosphorus oxychloride.

Step E

Step E can be achieved by various known techniques for removing a protective group of a mercapto group. For example, alkali hydrolysis is employed for removal of an acyl group, and a treatment with trifluoroacetic acid, trifluoromethanesulfonic acid, etc. is employed for removal of a trityl group, a p-methoxybenzyl group, etc.

The thus prepared compound of formula (II) may be reacted with the compound of formula (III) without being isolated from the reaction mixture.

The compounds of formula (I) according to the present invention are new and exhibit excellent antibacterial activity and are useful as drugs for treating and preventing bacterial infectious diseases, such as respiratory infectious diseases, urinary infectious diseases, suppurative diseases, and surgical infectious diseases.

The compounds of formula (I) are non-orally administered by, for example, intravenous injection, intramuscular injection or as suppositories, etc., or orally administered in the form of tablets, powders, capsules, syrups, etc. The compound of formula (I) can be formulated into these dosage forms by various known methods. For example, the compound is mixed with generally employed additives, such as adjuvants, wetting agents, emulsifying agents, binders, vehicles, and the like. The dose of the compound is decided depending on the age, sex, body weight, and difference in susceptibility of a patient, the route, time, and interval of administration, the degree of symptoms, the physical condition of a patient, the properties, kind, and active ingredients of the preparation, and the like. In general, the compound is preferably administered at a dose ranging from 1 to 100 mg/kg per day in 2 to 4 divided doses (5 to 30 mg/kg/dose).

The in vitro antibacterial activity of the compound of the present invention was determined according to an agar plate dilution method as follows. A test microorganism was cultured in a Mueller-Hinton's medium overnight, and a loopful of the microbial cells was inoculated to a Mueller-Hinton-agar medium ($10^6$ CFU/ml) containing the test compound in a prescribed concentration and cultured at 37° C. for 16 hours to obtain a minimum growth inhibition concentration (MIC; µg/ml). As a result, MIC of the compound of Example 4 hereinafter described against *S. aureus* 209 NIHJ JC-1 was 0.1 µg/ml.

The present invention is no illustrated in greater detail by way of Examples and Reference Examples, but it should be understood that the present invention is not deemed to be limited thereto. Abbreviations used herein have the following meanings.

Boc: t-butoxycarbonyl group
PMB: p-methoxybenzyl group
Bn: benzyl group
Ms: mesyl group
PNB: p-nitrobenzyl group Ph: phenyl group
Me: methyl group
Et: ethyl group

EXAMPLE 1

(5R,6S)-2-[(3RS,5S)-5-dimethylcarbamoyl-2-iminopyrrolidin-3-yl]thio-6-[(1R)-1-hydroxyethyl]-1-carbapen-2-em-3-carboxylic acid

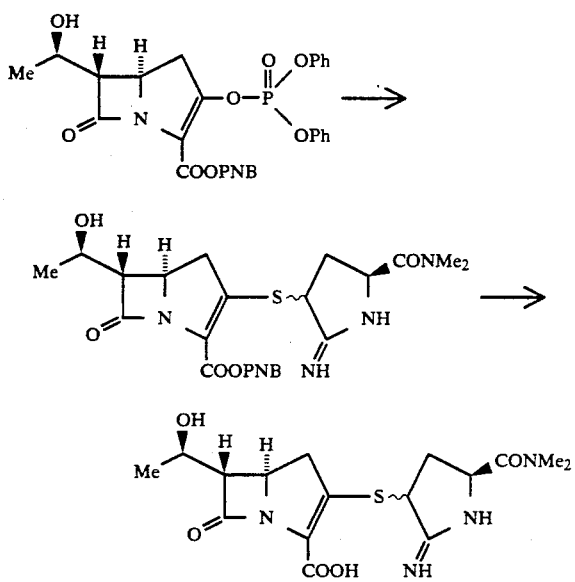

581 mg (1 mmol) of p-nitrobenzyl (5R,6S)-2-diphenylphosphoryloxy-6-[(1R)-1-hydroxyethyl]-1-carbapen-2-em-3-carboxylate was dissolved in 2 ml of DMF, and a solution of 565 mg (1.02 mmol) of (3RS,5S)-5-dimethylcarbamoyl-2-imino-3-mercaptopyrrolidine trifluoromethanesulfonate in DMF (2 ml) was added thereto at −50° C. under nitrogen atmosphere. Then, a solution of 0.178 ml (1 mmol) of diisopropylethylamine in DMF (1 ml) was added thereto, and the mixture was stirred for 30 minutes at the same temperature. 40 ml of THF and 40 ml of 0.1 M phosphate buffer (pH 7.0) were added to the reaction mixture. Then, mg of 10% palladium-carbon was added thereto, and the mixture was subjected to catalytic hydrogenation under about 3.1 kg/cm² at room temperature for 1.5 hours. After the reaction mixture was filtered, the filtrate was washed 5 times with chloroform and concentrated in order to remove organic solvents contained. The solution was purified by reversed phase column chromatography (Chemco LC-SORB®, SP-B-ODS, elution with water −10% methanol-water), and fractions containing the product were freeze-dried to obtain 174 mg (yield: 45.5%) of the above-identified compound.

IR (KBr) cm⁻¹: 3400, 1760, 1700, 1640, 1400.

UV $\lambda_{max}$ (0.1 M 3-morpholinopropanesulfonate buffer, pH 7.0): 297 nm ($\epsilon$=3,067)

NMR (D₂O) δ: 1.24 (3H,d,J=7Hz), 2.46–2.74 (1H,m), 2.74–3.26 (3H,m), 2.88 (3H,s), 3.00 (3H,s), 3.32–3.46 (1H,m), 4.06–4.26 (2H,m), 4.26–4.46 (2H,m), 4.46–4.66 (1H,m), 4.88–5.04 (1H,m).

EXAMPLE 2

(1R,5S,6S)-2-[(3RS,5S)-5-dimethylcarbamoyl-2-iminopyrrolidin-3-yl]thio-6-[(1R)-1-hydroxyethyl]-1-methylcarbapen-2-em-3-carboxylic acid

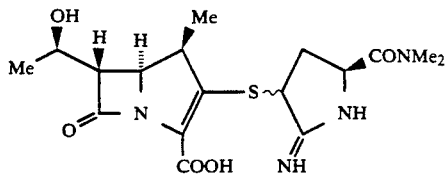

The same operation as in Example 1 was conducted by using 323 mg of (3RS,5S)-5-dimethylcarbamoyl-2-imino-3-mercaptopyrrolidine trifluoromethanesulfonate and 325 mg of p-nitrobenzyl (1R,5S,6S)-2-diphenylphosphoryloxy-6-[(1R)-1-hydroxyethyl]-1-methyl-carbapen-2-em-3-carboxylate, whereby 44.9 mg (yield: 20.7%) of the above-identified compound was obtained.

IR (KBr) cm⁻¹: 3420, 1755, 1700, 1650, 1400.

UV $\lambda_{max}$ (0.1 M 3-morpholinopropanesulfonate buffer, pH 7.0): 295 nm ($\epsilon$=3,814).

NMR (D₂O) δ: 1.26 (3H,d,J=7Hz), 1.31 (3H,d,J=7Hz), 2.33–2.73 (1H,m), 2.95 (3H,s), 3.05 and 3.07 (total 3H,s×2), 2.79–3.37 (1H,m), 3.37–3.45 (1H,m), 3.45–3.55 (1H,m), 4.15–4.33 (2H,m), 4.59–4.73 (1H,m), 4.91–5.13 (1H,m).

EXAMPLE 3

(1R,5S,6S)-2-[(3RS,5S)-2-dimethylamino-5-dimethylcarbamoyl-1-pyrrolin-3-yl]thio-6-[(1R)-1-hydroxyethyl-1-methylcarbapen-2-em-3-carboxylic acid

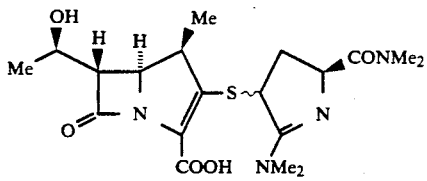

The same operation as in Example 1 was conducted by using 176 mg of (3RS,5S)-2-dimethylamino-5-dimethylcarbamoyl-3-mercapto-1-pyrroline trifluoromethanesulfonate and 124 mg of p-nitrobenzyl (1R,5S,6S)-2-diphenylphosphoryloxy-6-[(1R)-1-hydroxyethyl]-1-methylcarbapen-2-em-3-carboxylate; whereby 26.3 mg (yield: 29.6%) of the above-identified compound was obtained.

IR (KBr) cm⁻¹: 3450, 1760, 1690, 1650, 1600, 1400.

UV $\lambda_{max}$ (0.1 M 3-morpholinopropanesulfonate buffer, pH 7.0): 295 nm ($\epsilon$=1,613).

NMR (D₂O) δ: 1.29 (6H,d,J=7Hz), 2.25–2.73 (1H,m), 2.94 (3H,s), 3.05 and 3.11 (total 3H,s×2), 3.16, 3.19, 3.30 and 3.38 (total 6H,s×4), 2.74–3.36 (1H,m), 3.36–3.77 (2H,m), 4.03–4.35 (2H,m), 5.03–5.35 (1H,m).

EXAMPLE 4

(5R,6S)-2-[(3RS,5S)-5-carbamoyl-2-iminopyrrolidin-3-yl]thio-6-(1R)-1-hydroxyethyl]-1-carbapen-2-em-3-carboxylic acid

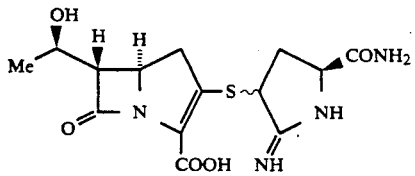

The same operation as in Example 1 was conducted by using 134 mg (0.365 mmol) of (3RS,5S)-5-carbamoyl-2-imino-3-mercaptopyrrolidine trifluoromethanesulfonate and 212 mg (0.365 mmol) of p-nitrobenzyl (5R,6S)-2-diphenylphosphoryloxy-6-[(1R)-1-hydroxyethyl]-1-carbapen-2-em-3-carboxylate, whereby 28.2 mg (yield: 21.8%) of the above-identified compound was obtained.

IR (KBr) cm$^{-1}$: 3420, 1740, 1700, 1630.

UV $\lambda_{max}$ (0.1 M 3-morpholinopropanesulfonate buffer, pH 7.0): 297 nm ($\epsilon$=3,569)

NMR (D$_2$O) δ: 1.24 (3H,d,J=6Hz), 2.50–3.00 (2H,m), 3.00–3.30 (2H,m), 3.30–3.50 (1H,m), 4.00–4.40 (2H,m).

EXAMPLE 5

(1R,5S,6S)-2-[(3RS,5S)-5-carbamoyl-2-iminopyrrolidin-3-yl]thio-6-[(1R)-1-hydroxvethyl]-1-methylcarbapen-2-em-3-carboxylic acid

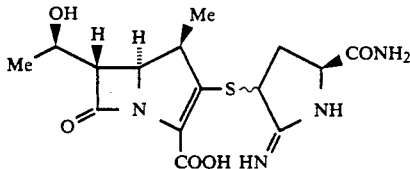

The same operation as in Example 1 was conducted by using 56.7 mg (0.183 mmol) of (3RS,5S)-5-carbamoyl-2-imino-3-mercaptopyrrolidine trifluoromethanesulfonate and 109 mg (0.183 mmol) of p-nitrobenzyl (1R,5S,6S)-2-diphenylphosphoryloxy-6-[(1R)-1-hydroxyethyl]-1-methylcarbapen-2-em-3-carboxylate, whereby 17.2 mg (yield: 25.5%) of the above-identified compound was obtained.

IR (KBr) cm$^{-1}$: 3400, 1750, 1700, 1635, 1620.

UV $\lambda_{max}$ (0.1 M 3-morpholinopropanesulfonate buffer, pH 7.0): 297 nm ($\epsilon$=5,029).

NMR (D$_2$O) δ: 1.11 (3H,d,J=7Hz), 1.22 (3H,d,J=7Hz), 2.50–2.70 (1H,m), 2.70–3.50 (3H,m), 4.10–4.30 (2H,m).

EXAMPLE 6

(1R,5S,6S)-2-[(3RS,5S)-5-carbamoyl-2-dimethylamino-1-pyrrolin-3-yl]thio-6-[(1R)-1-hydroxyethyl]-1-methylcarbapen-2-em-3-carboxylic acid

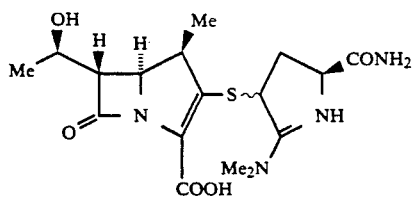

The same operation as in Example 1 was conducted by using 154 mg (0.345 mmol) of (3RS,5S)-5-carbamoyl-2-dimethylamino-3-mercapto-1-pyrroline trifluoromethanesulfonate and 205 mg (0.345 mmol) of p-nitrobenzyl (1R,5S,6S)-2-diphenylphosphoryloxy-6-[(1R)-1-hydroxyethyl]-1-methylcarbapen-2-em-3-carboxylate, whereby 18.6 mg (yield: 13.6%) of the above-identified compound was obtained.

IR (KBr) cm$^{-1}$: 3400, 1760, 1695, 1620.

UV $\lambda_{max}$ (0.1 M 3-morpholinopropanesulfonate buffer, pH 7.0): 299 nm ($\epsilon$=2,752)

NMR (D$_2$O) δ: 1.10–1.30 (6H,m), 2.40–2.90 (2H,m), 3.12, 3.18 and 3.21 (total 6H, s×3), 2.90–3.80 (3H,m), 4.10–4.30 (2H,m), 4.50–4.70 (1H,m).

EXAMPLE 7

(3RS,5S)-5-dimethylcarbamoyl-2-imino-3-mercaptopyrrolidine trifluoromethanesulfonate

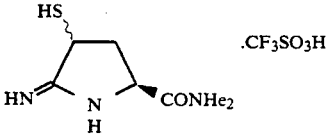

EXAMPLE 7-1

(3R,5S)-5-benzyloxycarbonyl-3-mesyloxypyrrolidin-2-one

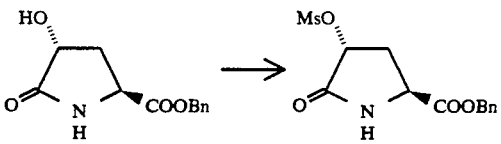

14.6 g (62.1 mmol) of (3R,5S)-5-benzyloxycarbonyl-3-hydroxypyrrolidin-2-one was dissolved in 135 ml of dichloromethane, and 10.7 ml (77 mmol) of triethylamine and then 5.62 ml (72.6 mmol) of mesyl chloride were added dropwise thereto under cooling with ice. After stirring for 30 minutes at the same temperature, the reaction mixture was washed with water, dried over anhydrous magnesium sulfate, and the solvent was distilled off. The residue was triturated with ether to obtain 15.2 g (yield: 78.2%) of the above-identified compound.

mp: 135° C.

IR (KBr) cm$^{-1}$: 3325, 1725, 1355, 1220, 1170.

NMR (CDCl$_3$) δ: 2.52–2.93 (2H,m), 3.26 (3H,s), 4.38 (1H,dd,J=3,9Hz), 5.23 (2H,s), 5.16–5.31 (1H,m), 6.42 (1H,brs), 7.40 (5H,s)

EXAMPLE 7-2

(3RS,5S)-5-dimethylcarbonyl-3-p-methoxybenzylthiopyrrolidin-2-one

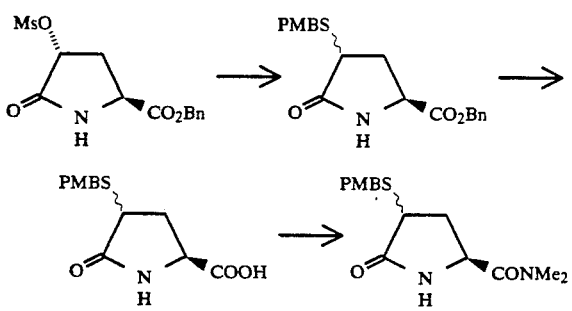

16.3 g (52.1 mmol) of (3R,5S)-5-benzyloxycarbonyl-3-mesyloxypyrrolidin-2-one was dissolved in 82 ml of DMF, and 7.95 ml (57.3 mmol) of p-methoxybenzylmercaptan was added to the solution under cooling with ice, then 8.48 ml (56.7 mmol) of DBU was added dropwise thereto. The mixture was stirred for 15 minutes at room temperature. Ethyl acetate was added to the reaction mixture, which was washed sequentially with water, 1 N HCl, a saturated sodium hydrogencarbonate aqueous solution and a saturated sodium chloride aqueous solution. The ethyl acetate solution was dried over anhydrous magnesium sulfate and the solvent was distilled off to obtain 21.6 g of (3RS,5S)-5-benzyloxycarbonyl-3-p-methoxybenzylthiopyrrolidin-2-one as an oily substance. This oily substance was dissolved in 122 ml of methanol, and 36.5 ml of 2N NaOH was added thereto under cooling with ice, and then the mixture was stirred for 1 hour at the same temperature. After the reaction mixture was washed twice with ethyl acetate, the aqueous layer was adjusted to pH 2.0 with 2N HCl, extracted with ethyl acetate, dried over anhydrous magnesium sulfate, and the solvent was distilled off. The residue was triturated with isopropyl ether to obtain 10.6 g of (3RS,5S)-3-p-methoxybenzylthio-2-oxopyrrolidin-5-carboxylic acid. This was dissolved in 348 ml of THF, and 6.17 g (75.7 mmol) of dimethylamine hydrochloride and 11.5 g (94.3 mmol) of 4-dimethylaminopyridine were added thereto under cooling with ice. And then, a solution of 11.7 g (56.8 mmol) of DCC in 37 ml of THF was added dropwise thereto. The mixture was stirred for 3 hours at the same temperature, and then for 1 day at room temperature. After the precipitate was filtered off, ethyl acetate was added to the filtrate, which was washed with 1N HCl. The solution was dried over anhydrous magnesium sulfate, and the solvent was distilled off. The residue was purified by silica gel column chromatography (Wakogel® C-300, elution with 1–2% methanol-chloroform) to obtain 5.33 g (yield: 28.4%) of (3S,5S)-5-dimethylcarbamoyl-3-p-methoxybenzylthiopyrrolidin-2-one as an oil and 4.41 g (yield: 23.5%) of (3R,5S)-5-dimethylcarbamoyl-3-p-methoxybenzylthiopyrrolidin-2-one as a powder.

(3S,5S) isomer

IR (KBr) cm$^{-1}$: 3250, 2930, 1700, 1640, 1510, 1245.

NMR (CDCl$_3$) δ: 2.02–2.03 (1H,m), 2.32–2.54 (1H,m), 2.99 (3H,s), 3.02 (3H,s), 3.40 (1H,dd, J=5,9Hz), 3.82 (3H,s), 3.86 and 4.14 (2H,ABq,J=13Hz), 4.56 (1H,t,J=7Hz), 6.40 (1H,brs), 6.88 (2H,d,J=9Hz), 7.36 (2H,d,J=9Hz).

[d]$^{25}_D$+126.1° (C=1.1,CHCl$_3$).

(3R,5S) isomer

IR (KBr) cm$^{-1}$: 3280, 2930, 1700, 1650, 1510, 1240.

NMR (CDCl$_3$) δ: 1.84–2.06 (1H,m), 2.61–2.90 (1H, m) 2.98 (6H,s), 3.37 (1H,t,J=9H), 3.81 (3H,s), 3.80 and 4.13 (2H,ABq,J=13Hz), 4.81 (3H,s), 4.39 (1H,t,J=8Hz), 6.21 (1H,brs), 6.87 (2H,d,J=9Hz), 7.33 (2H,d,J=9Hz).

[d]$^{25}_D$−109° (C=1,CHCl$_3$).

EXAMPLE 7-3

(3S,5S)-5-dimethylcarbamoyl-2-ethoxy-3-p-methoxybenzylthio-1-pyrroline

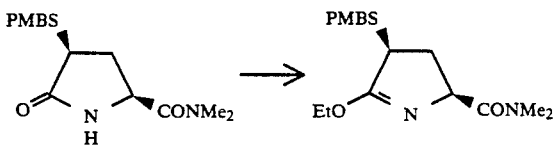

5.29 g (17.2 mmol) of (3S,5S)-5-dimethylcarbamoyl-3-p-methoxybenzylthiopyrrolidin-2-one was dissolved in 10 ml of dichloromethane, and 31 ml (20 mmol) of a solution of triethyloxonium tetrafluoroborate in dichloromethane (0.646 mmol/ml) was added thereto under cooling with ice. Then, the mixture was stirred for 2.5 hours at room temperature. The reaction mixture was added to 74 ml of an ice-cooled aqueous solution containing 3.7 g of potassium carbonate, and dichloromethane layer was separated, washed with water and dried over anhydrous magnesium sulfate. The solvent was distilled off, and the residue was purified by silica gel column chromatography (Wakogel® C-300, elution with 1–2% methanol-chloroform) to obtain 2.54 g (yield: 44.0%) of the above-identified compound as an oil.

IR (KBr) cm$^{-1}$: 3400, 2925, 1640, 1510, 1310, 1240, 1030.

NMR (CDCl$_3$) δ: 1.36 (3H,t,J=7Hz), 1.82–2.12 (1H,m), 2.62–3.00 (1H,m), 2.97 (3H,s), 3.19 (3H,s), 3.70–4.10 (3H,m), 3.81 (3H,s), 4.29 (2H,q,J=7Hz], 4.76 (1H,dd,J=5,8Hz), 6.86 (2H,d,J=9Hz), 7.28 (2H,d,J=9Hz).

EXAMPLE 7-4

(3R,5S)-5-dimethylcarbamoyl-2-ethoxy-3-p-methoxybenzylthio-1-pyrroline

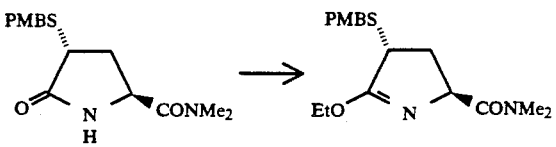

2.19 g (yield: 45.9%) of the above-identified compound was synthesized from 4.38 g of (3R,5S)-5-dimethylcarbamoyl-3-p-methoxybenzylthiopyrrolidin-2-one in the same manner as in Example 7-3).

IR (KBr) cm$^{-1}$: 3420, 2925, 1640, 1510, 1310, 1240, 1030.

NMR (CDCl$_3$) δ: 1.35 (3H,t,J=7Hz), 2.41–2.67 (2H,m) 3.01 (3H,s), 3.21 (3H,s), 3.62 (1H,t, J=9Hz), 3.81 (3H,s), 3.71–4.10 (2H,m) 4.25 (2H,q,J=7Hz), 4.59 (1H,t,J=7Hz), 6.87 (2H,d,J=8Hz), 7.31 (2H,d,J=8Hz).

EXAMPLE 7-5

(3RS,5S)-5-dimethylcarbamoyl-2-imino-3-p-methoxybenzylthiopyrrolidine

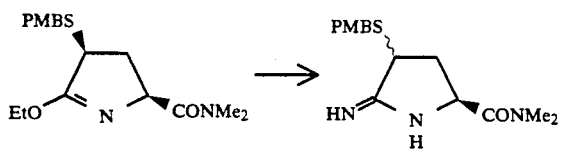

672 mg (2 mmol) of (3S,5S)-5-dimethylcarbamoyl-2-ethoxy-3-p-methoxybenzylthio-1-pyrroline and 118 mg (2.21 mmol) of ammonium chloride were dissolved in 34 ml of methanol, and the mixture was refluxed for 15 hours The solvent distilled off, and the residue was dissolved in water. The solution was washed twice with ethyl acetate. The ethyl acetate layer contains the unreacted material which became a mixture of 3R and 3S isomers because of isomerization during the reaction. The aqueous layer was adjusted to pH 10 with 2N NaOH and extracted with ethyl acetate. The ethyl acetate solution was washed with water and dried over anhydrous magnesium sulfate. The solvent was distilled off to obtain 129 mg (yield: 21%) of the above-identified compound as an oil. The same reaction was repeated twice by using the unreacted material contained in the above-mentioned ethyl acetate layer, whereby a total of mg (yield: 55.7%) of the desired product was obtained.

IR (KBr) cm$^{-1}$: 3400, 2920, 1640, 1620, 1510, 1240, 1030.

NMR (CDCl$_3$) δ: 1.95–3.00 (2H,m), 2.95 and 3.01 (total 3H,s×2), 3.21 and 3.23 (total 3H,s×2), 3.71 and 3.85 (2H,ABq,J=14H), 3.81 (3H,s), 4.00–4.22 (1H,m), 4.52–4.85 (1H,m), 6.85 and 6.87 (total 2H,d×2, each J=8Hz), 7.26 (2H,d,J=8Hz)

The same 3RS product was also obtained by the same reaction using the 3R isomer as a starting material.

EXAMPLE 7-6

(3RS,5S)-5-dimethylcarbamoyl-2-imino-3-mercaptopyrrolidine trifluoromethanesulfonate

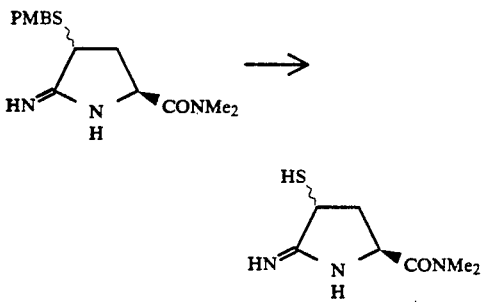

340 mg (1.11 mmol) of (3RS,5S)-5-dimethylcarbamoyl-2-imino-3-p-methoxybenzylthiopyrrolidine was dissolved in 0.2 ml of anisole and 4 ml of trifluoroacetic acid, and 0.5 ml of trifluoromethanesulfonic acid was added thereto under cooling with ice. Then, the mixture was stirred for 30 minutes at the same temperature. The solvent was distilled off, and the residue was washed with isopropyl ether to obtain 617 mg of the above-identified compound as a crude oil.

IR (KBr) cm$^{-1}$: 3400, 2550, 1710, 1650, 1250, 1030, 640.

NMR (CDCl$_3$) δ: 1.80–3.00 (2H,m), 2.89 and 2.91 (total 3H, each s), 3.03 (3H,s), 4.17–4.37 (1H,m), 4.83–5.17 (1H,m).

EXAMPLE 8

(3RS,5S)-2-dimethylamino-5-dimethylcarbamoyl-3-mercapto-1-pyrroline trifluoromethanesulfonate

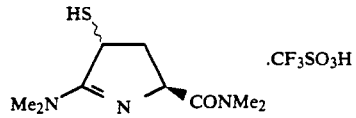

EXAMPLE 8-1

(3RS,5S)-2-dimethylamino-5-dimethylcarbamoyl-3-p-methoxybenzylthio-1-pyrroline

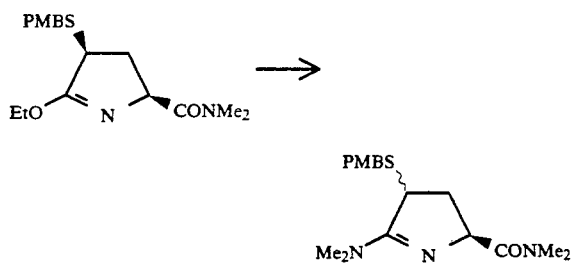

336 mg (1 mmol) of (3S,5S)-5-dimethylcarbamoyl-2-ethoxy-3-p-methoxybenzylthio-1-pyrroline and 89.5 mg (1.1 mmol) of dimethylamine hydrochloride were dissolved in 17 ml of methanol, and the mixture was refluxed for 15 hours. The solvent was distilled off, and the residue was dissolved in water and extracted twice with ethyl acetate. The ethyl acetate layer contains the unreacted material which became a mixture of 3R and 3S isomers because of isomerization during the reaction. The aqueous layer was adjusted to pH with 2N NaOH and extracted with ethyl acetate. The ethyl acetate solution was washed with water and dried over anhydrous magnesium sulfate. The solvent was distilled off to obtain the above-identified compound as an oil. The same reaction was repeated 3 times by using the unreacted material contained in the above-mentioned ethyl acetate layer, whereby a total of 149 mg (yield: 44.5%) of the desired product was obtained.

IR (KBr) cm$^{-1}$: 2920, 1640, 1605, 1510, 1245.

NMR (CDCl$_3$) δ: 1.90–3.00 (2H,m), 2.89 and 2.91 (total 6H,s×2), 2.99 (3H,s), 3.23 (3H,s), 3.63–4.01 (3H,m), 3.82 (3H,s), 4.65–4.86 (1H,m), 6.87 (2H,d,J=8Hz), 7.26 (2H,d,J=8Hz).

EXAMPLE 8-2

(3RS,5S)-2-dimethylamino-5-dimethylcarbamoyl-3-mercapto-1-pyrroline trifluoromethanesulfonate

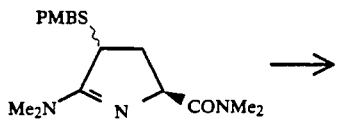

-continued

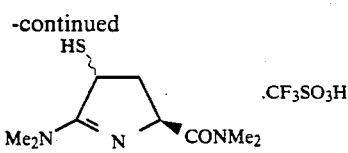

The same operation as in Example 7-6) was conducted by using 149 mg of (3RS,5S)-2-dimethylamino-5-dimethylcarbamoyl-3-p-methoxybenzylthio-1-pyrroline, whereby 373 mg of the above-identified compound was obtained as a crude oil.

IR (KBr) cm$^{-1}$: 3400, 2550, 1690, 1640, 1250, 1030, 640.

NMR (D$_2$O) δ: 2.13–3.00 (2H,m), 2.95 (3H,s) 3.11 (3H,s), 3.17 (3H,s), 3.31 (3H,s).

EXAMPLE 9

(3RS,5S)-5-carbamoyl-2-dimethylamino-3-mercapto-1-pyrroline trifluoromethanesulfonate

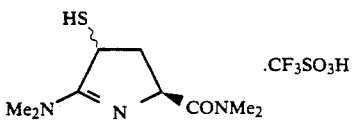

EXAMPLE 9-1

(3RS,5S)-5-carbamoyl-2-dimethylamino-3-p-methoxybenzylthio-1-pyrroline

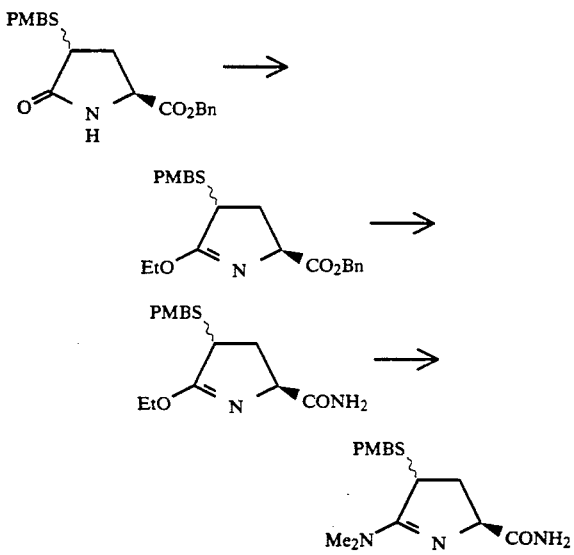

17.6 g (47.4 mmol) of (3RS,5S)-5-benzyloxycarbonyl-3-p-methoxybenzylthiopyrrolidin-2-one obtained by Example 7-2) was dissolved in 27 ml of dichloromethane, and 86 ml (55.6 mmol) of a solution of triethyloxonium tetrafluoroborate in dichloromethane (0.646 mmol/ml) was added thereto under cooling with ice.

After the mixture was stirred for 6 hours at room temperature, additional 86 ml (55.6 mmol) of a solution of triethyloxonium tetrafluoroborate in dichloromethane was added thereto, and the mixture was stirred for 5 hours at room temperature. The reaction mixture was added to 410 ml of an ice-cooled aqueous solution containing 20.4 g of potassium carbonate, and the organic layer was separated, washed with water and dried over anhydrous magnesium sulfate. The solvent was distilled off, and the residue was purified by silica gel column chromatography (Wakogel ® C-300, elution with ethyl acetate-hexane system) to obtain 6.38 g (yield: 33.7%) of the desired product and 5.93 g of the unreacted starting material. 5.93 g of this unreacted starting material was treated in a similar manner as described above to obtain additional 3.92 g of the product. A total of 10.3 g (yield: 54.5%) of (3RS,5S)-5-benzyloxycarbonyl-2-ethoxy-3-p-methoxybenzylthio-1-pyrroline was obtained. This was dissolved in a saturated ammoniamethanol solution, and the solution was allowed to stand overnight at room temperature. After an insoluble material was filtered off, the solvent was distilled off, and the residue was purified by silica gel column chromatography (Wakogel ® C-300, elution with 2–3% methanol-chloroform) to obtain 4.63 g (yield: 58.3%) of (3RS,5S)-5-carbamoyl-2-ethoxy-3-p-methoxybenzylthio-1-pyrroline. 530 mg (1.72 mmol) of this compound and 154 mg (1.89 mmol) of dimethylamine hydrochloride were dissolved in methanol, and the mixture was refluxed for 15 hours. The solvent was distilled off, and ethyl acetate and water were added to the residue. Then, aqueous layer was separated and washed with ethyl acetate. (The ethyl acetate layer contains the unreacted compound.) The aqueous layer was adjusted to pH 10 with 2N NAOH and extracted with ethyl acetate. Then, the ethyl acetate solution was washed with water and dried over anhydrous magnesium sulfate, and the solvent was distilled off to obtain the above-identified compound. The same reaction was repeated 5 times by using the unreacted material contained in the methyl acetate layer, whereby a total of 220 mg (yield: 41.7%) of the above-identified compound was obtained.

IR (KBr) cm$^{-1}$: 3400, 2930, 1680, 1510, 1250.

NMR (CDCl$_3$) δ: 2.0–2.30, 2.5–2.8 (total, 2H, m×2) 2.91 and 2.93 (total 6H,s×2), 3.81 (3H,s), 3.40–4.00 (3H,m), 4.30–4.60 (1H,m), 5.42 (1H,brs), 6.86 (2H,d, J=8Hz), 6.98 (1H,brs), 7.24 (2H,d,J=8Hz).

EXAMPLE 9-2

(3RS,5S)-5-carbamoyl-2-dimethylamino-3-mercapto-1-pyrroline trifluoromethanesulfonate

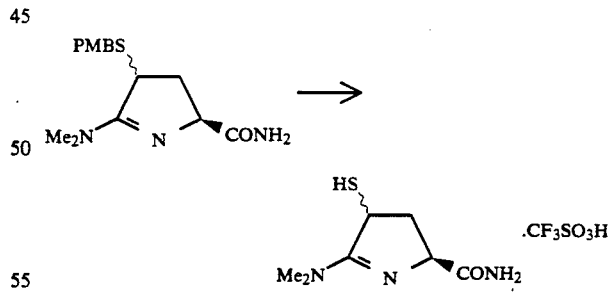

220 mg (0.717 mmol) of (3RS,5S)-5-carbamoyl-2-dimethylamino-3-p-methoxybenzylthio-1-pyrroline was dissolved in 0.13 ml of anisole and 2.6 ml of trifluoroacetic acid. Then, 0.32 ml of trifluoromethanesulfonic acid was added thereto under cooling with ice, and the mixture was stirred for 30 minutes at the same temperature. The solvent was distilled off, and the residue was washed with isopropyl ether and then with diethyl ether to obtain 320 mg of the above-identified compound as a crude oil.

IR (KBr) cm$^{-1}$: 3400, 1690, 1620, 1280, 1175, 1030, 640.

NMR (DMSO-d$_6$+D$_2$O) δ:2.40–2.890 (2H,m), 3.14 (3H,s) 3.26 (3H,s), 4.10–4.70 (2H,m).

EXAMPLE 10

(3RS,5S)-5-carbamoyl-2-imino-3-mercaptopyrrolidine trifluoromethanesulfonate

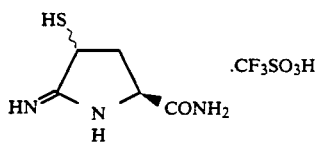

EXAMPLE 10-1

(3RS,5S)-5-carbamoyl-2-imino-3-p-methoxybenzylthiopyrrolidine

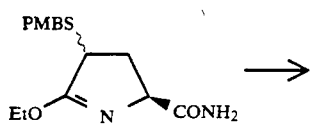

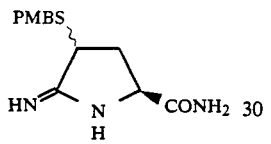

The same operation as in Example 7-5) was conducted by using 138 mg (0.448 mmol) of (3RS,5S)-5-carbamoyl-2-ethoxy-3-p-methoxybenzylthio-1-pyrroline obtained by Example 9-1) and 26.5 mg (0.495 mmol) of ammonium chloride, whereby 73.9 mg (yield: 59.1%) of the above-identified compound was obtained.

IR (KBr) cm$^{-1}$: 3450, 1640, 1520, 1240.

NMR (CDCl$_3$) δ: 2.00–3.00 (2H,m), 3.60–4.00 (3H,m) 3.80 (3H,s), 4.00–4.50 (1H,m), 5.57 (2H,brs), 6.50 (1H,brs), 6.70 (1H,brs), 6.86 (2H,d,J=8Hz), 7.23 (2H,d,J=8Hz).

EXAMPLE 10-2

(3RS,5S)-5-carbamoyl-2-imino-3-mercaptopyrrolidine trifluoromethanesulfonate

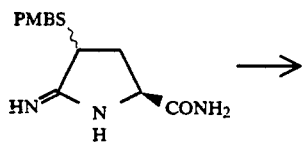

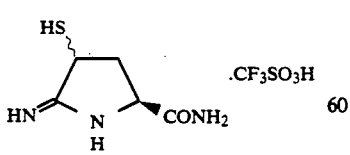

The same operation as in Example 9-2) was conducted by using 7.2 mg (0.259 mmol) of (3RS,5S)-5-carbamoyl-2-imino-3-p-methoxybenzylthiopyrrolidine, whereby 56.7 mg (yield: 70.8%) of the above-identified compound was obtained as a crude powder.

REFERENCE EXAMPLE 1

(3R,5S)-5-benzyloxycarbonyl-3-hydroxypyrrolidin-2-one

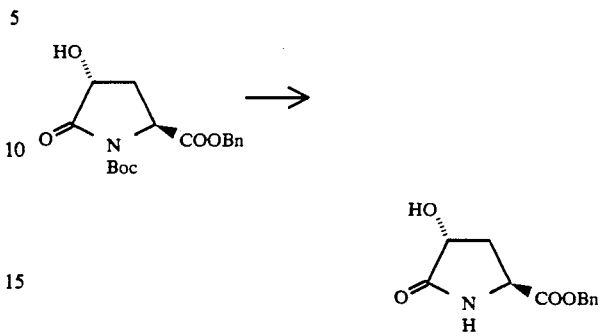

.10 g (29.9 mmol) of (3R,5S)-5-benzyloxycarbonyl-1-tert-butoxycarbonyl-3-hydroxypyrrolidin-2-one prepared by the procedure described in T. Ohta et al, Tetrahedron Letters, 29, 329 (1988) was dissolved in 32 ml of dichloromethane, and 3.5 ml of anisole was added thereto. Then, 32 ml of trifluoroacetic acid was added dropwise to the mixture under cooling with ice, and the mixture was stirred for 1 hour at the same temperature. The reaction mixture was concentrated under reduced pressure. Ethyl acetate and water were added to the residue and adjusted to ph 8.0 with 2N NaOH. The organic layer was separated, washed with a saturated sodium chloride aqueous solution and dried over anhydrous magnesium sulfate. The solvent was distilled off, and the residue was triturated with diethyl ether to obtain 4.76 g (yield: 67.7%) of the above-identified compound.

mp: 88° C. (decomp.).

IR (KBr) cm$^{-1}$: 3420, 3220, 1745, 1705, 1200.

NMR (CDCl$_3$) δ: 2.10–2.50 (1H,m), 2.50–2.80 (1H,m) 3.63 (1H,brs), 4.21–4.50 (2H,m), 5.19 (2H,s), 6.69 (1H,brs), 7.37 (5H,s).

[d]$^{25}{}_D$+33.5° (C=2.1,CHCl$_3$).

The compounds of formula (I) according to the present invention exhibit excellent antibacterial activity against Gram positive bacteria and Gram negative bacteria and are useful as an antibacterial agent.

While the invention has been described in detail and with reference to specific embodiments thereof, it will be apparent to one skilled in the art that various changes and modifications can be made therein without departing from the spirit and scope thereof.

What is claimed is:

1. A compound represented by formula (I):

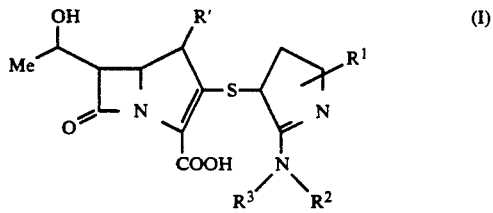

wherein R$^1$ represents a hydrogen atom or a methyl group; R$^2$ and R$^3$, which may be the same or different, each represents a hydrogen atom or a lower alkyl group; and R$^4$ represents a carboxyl group, a lower alkoxycarbonyl group, a carbamoyl group, a lower alkylcarbamoyl group, a di-lower alkylcarbamoyl group, or a carbonyl group substituted with a heterocyclic group selected from the group consisting of a 1-aziridinyl group, a 1-azetidinyl group, a 1-pyrrolidinyl group, a piperidino group, a morpholine group, a thiomorpholino group, a 1-piperazinyl group and a 4-lower alkyl-1-piperazinyl group, or a pharmaceutically acceptable salt or ester thereof.

2. The compound of claim 1, wherein $R^2$ and $R^3$ each represents a hydrogen atom; and $R^4$ represents a di-lower alkylcarbamoyl group.

3. The compound of claim 1, wherein the carbapenem skeleton has a (5R,6S,8R)-configuration or a (1R,5S,6S,8R)-configuration.

4. The compound of claim 1, wherein the compound is selected from the group consisting of (5R,6S)-2-[(3Rs,5S)-5-carbamoyl-2-iminopyrrolidin-3-yl]thio-6-[(1R)-1-hydroxyethyl]-1-carbapen-2-em-3-carboxylic acid, (1R,5S,6S)-2-[(3RS,5S)-5-carbamoyl-2-iminopyrrolidin-3-yl]thio-6-[(1R)-1-hyroxyethyl]-1-methylcarbapen-2-em-3carboxylic acid, (5R,6S)-2-[(3RS,5S)-5-carbamoyl-2-dimethylamino-1-pyrrolidin-3-yl]thio-6-[(1R)-1-hydroxyethyl]-1-carbapen-2-em-3-carboxylic acid, (1R,5S,6S)-2-[(3RS,5S)-5-carbamoyl-2-dimethylamino-1-pyrrolin-3-yl]thio-6-[(1R)-1-hydroxyethyl]-1-methylcarbapen-2-em-3-carboxylic acid, (5R,6S)-2-[(3RS,5S)-5-dimethylcarbamoyl-2-iminopyrrolidin-3yl]thio-6-[(1R)-1-hydroxyethyl]-1-carbapen-2-em-3-carboxylic acid, (1R,5S,6S)-2-[ (3RS,5S)-5-dimethylcarbamoyl-2-iminopyrrolidin-3yl]thio-6-[(1R)-1-hydroxyethyl]-1-methylcarbapen-2-em-3-carboxylic acid, (5R,6S)-2-[(3RS,5S)-2dimethylamino-5-dimethylcarbamoyl-1-pyrrolin-3-yl]thio-6-[(1R)-1-hydroxyethyl]-1-carbapen-2-em-3-carboxylic acid and [(1R,5S,6S)-2-[(3RS,5S)-2-dimethylamino-5-dimethylcarbamoyl-1-pyrrolin-3-yl]thio-6[(1R)-1-hydroxyethyl]-1-methylcarbapen-2-em-3-carboxylic acid.

5. The compound of claim 1, wherein the compound is (1R,5S,6S)-2-[(3RS,5S)-5-carbamoyl-2-iminopyrrolidin-3-yl] thio-6-[(1R)-1-hydroxyethyl]-1-methylcarbapen-2-em-3-carboxylic acid or (1R,5S,6S)-2-[(3RS,5S)-5-dimethylcarbamoyl-2-iminopyrrolidin-3yl]thio-6-[(1R)-1-hydroxyethyl]-1-methylcarbapen-2-em-3-carboxylic acid.

6. An antibacterial agent containing a compound represented by formula (I):

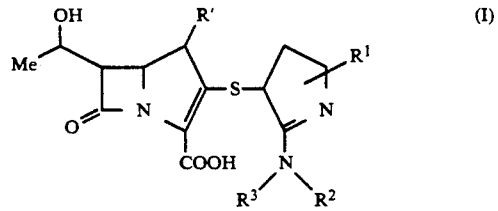

wherein $R^1$ represents a hydrogen atom or a methyl group; $R^2$ and $R^3$, which may be the same or different, each represents a hydrogen atom or a lower alkyl group; and $R^4$ represents a carboxyl group, a lower alkoxycarbonyl group, a carbamoyl group, a lower alkylcarbamoyl group, a di-lower alkylcarbamoyl group, or a carbonyl group substituted with a heterocyclic group selected from the group consisting of a 1-aziridinyl group, a 1-azetidinyl group, a 1-pyrrolidinyl group, a piperidino group, a morpholino group, a thiomorpholino group, a 1-piperazinyl group and a 4-lower alkyl-1-piperazinyl group, or a pharmaceutically acceptable salt or ester thereof as an active ingredient.

* * * * *